US005661014A

United States Patent [19]

Evans et al.

[11] Patent Number: 5,661,014

[45] Date of Patent: Aug. 26, 1997

[54] CHIRAL COMPOUNDS AND THEIR RESOLUTION SYNTHESIS USING ENANTIOSELECTIVE ESTERASES

[75] Inventors: Christopher Thomas Evans, Hendon, Nr Royston; Raymond McCague, Milton; Stephen John Clifford Taylor, Ely, all of United Kingdom

[73] Assignee: Chiroscience Limited, Cambridge, United Kingdom

[21] Appl. No.: 452,677

[22] Filed: May 30, 1995

Related U.S. Application Data

[63] Continuation-in-part of Ser. No. 193,132, Feb. 18, 1994, abandoned.

[30] Foreign Application Priority Data

| | | | |
|---|---|---|---|
| Aug. 22, 1991 | [GB] | United Kingdom | 9118149 |
| Aug. 22, 1991 | [GB] | United Kingdom | 9118151 |
| May 27, 1994 | [GB] | United Kingdom | 9410721 |

[51] Int. Cl.$^6$ .................... C12P 17/12; C12P 17/14; C12P 17/10

[52] U.S. Cl. .................... 435/122; 435/120; 435/121; 435/128; 435/280; 546/250

[58] Field of Search .................... 435/122, 280, 435/120, 121, 128

[56] References Cited

FOREIGN PATENT DOCUMENTS

| | | |
|---|---|---|
| 0 258 617 | 3/1988 | European Pat. Off. . |
| 32 24 019 | 2/1984 | Germany . |

OTHER PUBLICATIONS

G. Ramos et al., "Application of Microbes and Microbial Esterases to the Preparation of Optically Active N–Acetylindoline–2–Carboxylic Acid", *Agric. Biol. Chem.* 51(7): 1833–1838 (1987).

R. McCague et al., "Synthesis of the Aromatase Inhibitor 3–Ethyl–3–(4–pyridyl)piperidine–2,6–dione and its Enantiomers", *J. Chem. Soc. Perkin Trans. I* pp. 196–198 (1989).

A. Boss et al., "A Concise Synthesis of Racemic Pyridoglutethimide and its Resolution Using Chiral Stationary Phase HPLC", *Tetrahedron* 45(18): 6011–6016 (1989).

*Primary Examiner*—David B. Springer
*Attorney, Agent, or Firm*—Foley & Lardner

[57] ABSTRACT

Enantiomeric glutarimides such as aminoglutethimide and rogletimide are prepared by cyclisation of a corresponding ester-nitrile which is a good substrate for biotransformation with an enantiospecific esterase.

22 Claims, No Drawings

CHIRAL COMPOUNDS AND THEIR RESOLUTION SYNTHESIS USING ENANTIOSELECTIVE ESTERASES

REFERENCE TO A RELATED APPLICATION

This application is a continuation-in-part of commonly-assigned application Ser. No. 08/193,132, filed Feb. 18, 1994, now abandoned.

FIELD OF THE INVENTION

This invention relates to chiral compounds that are useful as intermediates in the synthesis of pharmaceutically-active glutarimides, and to their resolution.

BACKGROUND OF THE INVENTION

Racemates of 3,3-disubstituted glutarimides such as 3-ethyl-3-(4-aminophenyl)piperidine-2,6-dione (aminoglutethimide) and 3-ethyl-3-(4-pyridyl)piperidine-2,6-dione (rogletimide; also known as pyridoglutethimide, and sometimes described herein as 4-PG) have been shown to be effective for the treatment of hormone-dependent breast cancer; see Smith et al, Lancet ii:646 (1978), and Foster et al, J. Med. Chem. 28:200 (1985). The mode of action of these compounds is considered to be inhibition of the enzyme aromatase that catalyses the formation of estrogens from androgens; thus the compounds inhibit tumours whose growth is promoted by estrogens.

Graves et al, Endocrinology 105:52 (1979), disclose that the (R)-enantiomers of these compounds are much more potent as inhibitors of aromatase than the (S)-enantiomers. Therefore, it is likely that the (R)-enantiomers are essentially the active components in the racemates, and so a process for their preparation is desirable.

The separate enantiomers of aminoglutethimide and rogletimide have been prepared respectively by repeated recrystallisation of tartrate salts, and by using camphor-derived chiral auxiliaries; see Finch et al, Experimentia 31:1002 (1975), and McCague et al. J. Chem. Soc. Perkin Trans. 1:196–8 (1989). Separation has also been accomplished by chromatography on chiral stationary phases based on tartramides or triacylcelluloses. However, these methods are not amenable to economic large-scale working appropriate for the manufacture of the bulk single-enantiomer drug substance.

Since the filing of the above-identified copending application, McCague et al, J. Med. Chem. 35:3699–3704 (1992), disclose that derivatives of rogletimide, including 5-alkyl derivatives, may have improved aromatase inhibition activity. Aromatase inhibition by the enantiomers of aminoglutethimide, rogletimide and also cyclohexylaminoglutethimide, in vitro, is reported by Ogbunude et al, Chirality 6:623–626 (1994).

SUMMARY OF THE INVENTION

According to the present invention, a process for the manufacture of such glutarimide compounds, is by way of biocatalytic resolution of glutarate diesters or ester-nitriles, and then cyclisation. Only the less hindered ester function is hydrolysed by an appropriate biocatalyst, with a degree of enantiospecificity showing that the biocatalyst can distinguish aryl, ethyl and carboxylic ester or nitrile substituents borne on a quaternary carbon atom. While only moderate specificity was observed in the case of precursors of rogletimide, the biotransformation products were easily converted into rogletimide and means is provided to then increase the enantiomeric excess.

According to one aspect of the present invention, effective biocatalytic resolution, using available esterases, is possible using compounds of formula II. Good enantiospecificities have been obtained for resolution by way of biocatalytic hydrolysis of the ester function. Thus the appropriate enzyme is able to distinguish between substituents, e.g. aryl, ethyl and nitrile, borne on a quaternary carbon atom. More particularly, racemic formula II compound may be contacted with an enantiospecific esterase that enriches the mixture in terms of one enantiomer, by reacting with the other enantiomer to form the corresponding acid (II: R=H) which may be separated; partial enrichment may be enhanced by further resolution with a tartaric acid or conventional camphor-derived chiral auxiliary.

DESCRIPTION OF THE INVENTION

As a substrate for biotransformation, in formula II, R is an esterifying group, suitably an alkyl residue containing up to 10 carbon atoms, e.g. straight-chain alkyl, branched alkyl, arylalkyl and aryl optionally substituted with, for example, halogen. For the purpose of the invention, the simplest alkyl group (R=methyl or ethyl) is adequate, and in terms of simplifying the chemical processing, is preferred. For cyclisation, after biotransformation, R may be H; alternatively, depending on the enantiomer that is desired, R may be unchanged.

Q is COOR' or CN. R' may be the same as or different to R. Again R' is preferably methyl or ethyl. Q as CN is often preferred.

X and Z are each H or an organic group. X may be, for example, $C_{1-10}$ alkyl such as ethyl. Z is preferably H or a $C_{1-10}$ alkyl group, e.g. to give a 5-alkyl product. The compound of formula I may be any aromatase inhibitor such as aminoglutethimide (I: X=ethyl, Y=4-aminophenyl, Z=H), 4-P (I: X=ethyl, Y=4-pyridyl, Z=H) or any analogue, e.g. the specific compounds described above, or isopropylglutethimide. The compound of formula I may also be an intermediate for hypotensive agents such as verapamil. Y is thus defined; in general, Y (or Ar in the Chart) is a cyclic group, either an aryl, carbocyclic or heterocyclic radical, e.g. of up to 12 C atoms, including any substituents. Y is preferably dimethoxyphenyl, 4-pyridyl, 4-aminophenyl (optionally N-protected), isopropylphenyl or cyclohexylphenyl. Especially as a precursor to Y-aminophenyl, e.g. by catalytic hydrogenation, Y may also be nitrophenyl; (R)-3-ethyl-3-(4-nitrophenyl)piperidine-3,6-dione is a novel compound. Compounds of formula II in which Y is nitrophenyl give especially good biotransformation yields.

For the purpose of illustration only, the processes involved in the invention may be described with reference to the production of, say, enantiomeric 4-PG or enantiomeric aminoglutethimide, as outlined in Charts A and B, respectively. Chart A also shows how compounds of formula II (Q=COOR'; specifically formula 2) may be prepared by sequential alkylation of an alkyl 4-pyridyl-acetate (1) with iodoethane, e.g. in the presence of potassium t-butoxide and t-butyl alcohol and then with an alkyl acrylate. Compounds of formula II (specifically formula 6) may also be prepared by methods known to those skilled in the art, and exemplified below. One such method involves Michael addition to an acrylate ester (See Example 11).

The first step shown in Chart B is a characteristic of the invention. It is based on the use of biocatalysts that preferentially hydrolyse one enantiomer of a racemic ester (2) or nitrile (6) to give optically-enriched residual ester (2,7) and the acid (3,8). There are biocatalysts that produce the R-enantiomer (i.e. biocatalysts A in the Chart) and those that produce the S-enantiomer (biocatalysts B).

Suitable esterase activities may be available from acylase I (Aspergillus), esterase 30,000, Rhizopus Japonicus lipase, F3 lipase, A2 lipase (porcine pancreas), F6 lipase (from Candida), pig liver esterase, CE lipase and AY lipase. Cholesterol esterase is an alternative. Examples of biocatalysts A are *Candida cylindracae* lipase and enzyme activities of the genera in Examples 15 to 17.

Another example of a biocatalyst suitable for the biotransformation is the microbial strain P3U1, NCIMB 40517, which can produce R-acid of greater than 60% ee. Another suitable biocatalyst (of type B) is Trichosporon ENZA I-3, IMI 348917, whose characteristics, including its enantiospecificity for the conversion of aralkanoic acid esters into the acid, e.g. (S)-ketoprofen, are described in WO-A-9301489. α-Chymotrypsin is another suitable biocatalyst of category B.

A further biocatalyst is obtainable from any fungus of the type described in WO-A-9420634 for the enantiospecific hydrolysis of arylpropionic acid esters. A specific fungus of this type is *Ophiostoma novo-ulmi*, IMI 356050.

In specific examples of the biotransformation, when Q=CN, the phenylglutaronitrile ester (Ar=Ph, R=Me) with *Candida antarctica* lipase gave hydrolysis of the ester function to the acid with an enantiospecificity (E)=12. The nitrophenyl compound (Ar=4-nitrophenyl, R=Me) with α-chymotrypsin gave a transformation with E=39. The same substrate with esterase derived from the given fungus *Ophiostoma novo-ulmi* also gave transformation with the opposite specificity.

Conversion of the biotransformation products, which are readily separated by solvent extraction at neutral pH, into enantiomerically-enriched glutarimide is by conventional chemical techniques.

Conversion of the nitrile-esters to the glutarimides was accomplished easily under such conditions as heating with acid, e.g. a mixture of acetic acid and sulphuric acid, to provide the optically-active glutarimide compounds. These conditions are known in the conversion of racemic nitrile-esters into the racemic glutarimides, aminoglutethimide and rogletimide. Further, diesters (3) can be converted into (5) by heating with methanolic ammonia under pressure, and ester-acid (4) can be converted into (5) by heating with urea.

A further feature of the invention, especially in the case where Q=COOR', is the discovery of a process for producing essentially optically pure (5) from optically-enriched material derived from the biotransformation. It is therefore not essential that the biotransformation is absolutely specific for enantiomerically pure (5) to be manufactured. In an embodiment of this aspect of the invention, the optically-enriched (5) is converted (in the case of (R)-enantiomer) to the (1R)-(−)-10-camphorsulphonate salt and the salt recrystallised, for example from ethyl acetate:ethanol (10:1) whereupon material that has 0 to 50% ee in favour of (R or S)-glutarimide crystallises and leaves almost optically pure (5) salt in solution. Release of (5) from its salt and subsequent recrystallisation of the almost optically pure (5) can raise it to optical purity.

The following Examples illustrate the invention. Examples 8 and 11 illustrate the preparation of nitrile-esters (II) that are substrates for biotransformation, and Example 13 illustrates a relevant reduction. Examples 9, 12 and 15 to 17 illustrate biotransformations, and Examples 10 and 14 illustrate cyclisation reactions, in accordance with the invention. Examples 8 to 10, and Examples 11 to 14, provide different routes to the same product.

EXAMPLE 1

Growth of P3U1

The strain P3U1 was streaked onto nutrient agar plates and 5 g/l glucose, and incubated at 23° C. for 60 hours. Seed flasks, containing 150 ml growth medium (1 g/l $(NH_4)_2SO_4$; 2 g/l $KH_2PO_4$; 0.25 g/l $MgSO_4$; 0.1 g/l $CaCl_2$; 0.1 ml TES; 10 ml YE) per 500 ml flask, were inoculated from the nutrient agar plates and shaken at 23° C. 350 rpm for 24 hours. After 24 hours the optical density at 520 nm had reached 2.1. This was used to inoculate production fermenters (using a 10% inoculum): 1.5 l growth medium per Anglicon fermenter. These were grown at 23° C. with agitation; aeration was adjusted to keep the DOT above 50%. After 24 hours, the optical density at 520 nm had reached 2.5. The cells were then harvested at 5000 rpm for 10 min.

EXAMPLE 2

Biotransformation

The cell mass of P3U1 cells, harvested by centrifugation, was resuspended to an optical density of 2 (520 nm) in 10 mM $KH_2PO_4$, pH 7, containing yeast extract (5 g/l). (+)-Dimethyl 2-ethyl-2-(4-pyridyl)glutarate was added to a final concentration of 3 g/l. The cells were stirred at 23° C. without aeration or pH control. The enantiomeric excess (ee) of the substrate was monitored as the hydrolysis progressed (extraction of the diester into cyclohexane, followed by HPLC analysis of the cyclohexane layer on a Chiracel-OJ-column). After 72 hours, the ee of the remaining diester was 66%, and the biotransformation was harvested. Cells were removed by centrifugation, then diester extracted with ethyl acetate (3×1 l). The aqueous layer was then salted (10% weight NaCl) and the pH adjusted to 2.6 using conc. HCl. The product was then extracted with tetrahydrofuran (THF). The THF extracts were combined and evaporated under reduced pressure to give a brown oil, which was dried by azeotroping with toluene. The toluene solution was mixed with an equal volume of acetone, and the resulting precipitate of inorganic salts filtered off. The solvents were evaporated to give a brown oil which solidified on standing (yield 4.1 g). This was substantially R-2-ethyl-2-(4-pyridyl)glutaric acid 1-monomethyl ester.

EXAMPLE 3

Cyclisation

Cyclisation to the imide was effected by heating the product from Example 2 with an equal weight of urea for 20 min.

The product was partitioned between saturated sodium bicarbonate solution and ethyl acetate. The organic layer was dried ($MgSO_4$) and then evaporated to give crude 3-ethyl-3-(4-pyridyl)pyridine-2,6-dione (1.1 g). This was purified by flash chromatraphy on silica (eluting with 2:1 ether:triethylamine) to give pure enantiomerically enriched product (300 mg). The ee was found to be 56% as determined by HPLC on a Daicel Chiracel OJ column.

EXAMPLE 4 ee Enrichment

The purified imide from Example 3 (300 mg) was dissolved in ethyl acetate (10 ml). To this solution was added 1R-(−)-camphorsulphonic acid (1.1 mol equivalent, 352 mg). After 0.5 hr stirring at ambient temperature the mixture was brought to reflux and sufficient ethanol (3 ml) added to dissolve the solid. The clear solution was allowed to cool slowly to 5° C. after which the solid was removed by filtration (190 mg of racemic material). The enantiomeric excess of the product in the liquors was found to be 96.2%. The solvent was removed and the above recrystallisation process repeated. The final liquors contained R-3-ethyl-(4-pyridyl)piperidine-2,6-dione as its R-camphorsulphonate salt in 97.3% enantiomeric excess.

The R-enriched R-camphorsulphonate salt solution was concentrated to dryness then suspended in water (5 ml). The mixture was basified to pH 9 with 2N sodium hydroxide solution. The product was extracted into ethyl acetate and the organic extracts dried ($MgSO_4$). The final product was isolated and purified by flash chromatography as described in Example 3.

EXAMPLE 5

Biotransformation

Biotransformation on the same substrate as Example 2 was carried out in a baffled conical flask (500 ml) containing 0.1M $KH_2PO_4$ (100 ml) adjusted to pH 7, cyclohexane (100 ml), dimethyl ester (1 g) and *Mucor javanicus* lipase (700 mg). The flask contents were shaken at 23° C., and the ee of the remaining substrate in the cyclohexane layer monitored by HPLC. After 48 hours, the ee of the remaining substrate was 46% (enriched in the pro-R diester), at a conversion of 84%.

EXAMPLE 6

Biotransformation

The procedure described in Example 5 was carried out but using *Candida cylindracea* lipase as the biocatalyst. After 48 hr, the ee of the remaining diester was 66% in favour of S-enantiomer, at a conversion of 72%.

EXAMPLE 7

Biotransformation

ENZA I3 was inoculated from a freshly-grown YM (Difco) agar plate into 5 ml growth medium in a 20 ml container (the growth medium comprised 1 g/l $(NH_4)_2SO_4$, 2 g/l $KH_2PO_4$, 0.25 g/l $MgSO_4.7H_2O$, 0.1 g/l $CaCl_2.2H_2O$, 0.1 ml/l trace element solution, 10 g/l yeast extract, adjusted to pH 7.0 with sodium hydroxide). This was incubated at 23° C. for 24 hours with shaking. The cells were then spun and resuspended in 5 ml reaction buffer in a 20 ml container (the reaction buffer comprised 10 mM sodium phosphate, 5 g/l yeast extract (Fould Springer), 50 μl/l Tween 80, 3 g/l (+)-dimethyl 2-ethyl-2-(4-pyridylglutarate). This was shaken for 41 hours. The enantiomeric excess (ee) was measured by extraction of the diester into cyclohexane followed by HPLC analysis of the cyclohexane layer on a Chiracel-OJ column. After 22 hours, the residual diester had an ee of 54% in favour of the R configuration.

EXAMPLE 8

Methyl 4-cyano-4-(4-aminophenyl)hexanoate

A 3-necked round-bottomed flask was charged with methyl 4-cyano-4-(4-nitrophenyl)hexanoate (20.0 g), 90% ethanol (1000 ml) and $PtO_2$ (1.0 g). The vessel was then evacuated and charged with nitrogen. The mixture was stirred vigorously and subjected to $H_2$ at atmospheric pressure supplied via a balloon. The catalyst was removed by filtration through celite and the solvent removed under reduced pressure to give methyl 4-cyano-4-(4-aminophenyl)-hexanoate (18 g, 100%) as a viscous, brown oil.

EXAMPLE 9

A 500 ml jacketed biotransformation vessel as charged with 0.1M $KH_2PO_4$, pH 7.0 (250 ml) and methyl 4-(4-aminophenyl)4-cyanohexanoate (5.0 g, 20.3 mmol). *Candida cylindracea* lipase (CCL; 5.0 g) was introduced and the mixture was agitated using an overhead stirrer. Temperature was maintained at 30° C. with the aid of a thermocirculator and the pH controlled by a probe linked to an autotitrator. The biotransformation was allowed to proceed until 10 ml of 1M NaOH had been added (equivalent to 50% conversion). This took about 3 hours. At this point, the biotransformation was quenched by the addition of NaCl (25 g) and the resulting mixture was extracted with diethyl ether (250 ml×4). The pH of the aqueous solution was then adjusted to 3 using conc. HCl and the mixture extracted with ethyl acetate (400 ml×3). The extracts were pooled, dried and concentrated under reduced pressure, yielding 1.8 g (38%) of 4-(4-aminophenyl)-4-cyanohexanoic acid, enriched in the (R)-enantiomer, in the form of a brown oil. Without further treatment, a sample of this material was reacted as described in Example 10.

EXAMPLE 10

(R)-Aminoglutethimide 4-(4-Aminophenyl)-4-cyanohexanoic acid (Example 9; 1.8 g, 7.7 mmol), enriched in the (R)-enantiomer, was dissolved in glacial acetic acid (6.0 ml) contained in a 25 ml round-bottomed flask. The resulting mixture was heated to 60° C. with the aid of an oil bath followed by dropwise addition of conc. $H_2SO_4$ (3.0 ml). The solution was then heated to 100° C. and maintained there for 30 minutes before pouring onto ice (100 g). The pH is adjusted to 6 using 5M NaOH followed by extraction with dichloromethane (3×200 ml). The extracts were pooled, dried (over $MgSO_4$) and concentrated under reduced pressure, giving (R)-aminoglutethimide (1.75 g, 97%) as a brown oil. Chiral HPLC analysis (Chiralcel OJ column; mobile phase 1:1 n-heptane-isopropanol) indicated an ee of 78%.

EXAMPLE 11A 2-(4-Nitrophenyl)butyronitrile

A 3-necked round-bottomed flask was charged with conc. $HNO_3$ (240 ml) and cooled to 10° C. with the aid of an ice/acetone bath. Conc. $H_2SO_4$ (240 ml) was then added slowly so as to maintain the temperature below 30° C. 2-Phenylbutyronitrile (Aldrich, 110 ml) was introduced dropwise to the stirred solution over a period of 1 hour, maintaining the temperature below 20° C. The ice/acetone bath was then removed and the mixture stirred for a further 30 minutes at ambient temperature before pouring it onto crushed ice (100 g). The resulting mixture was extracted with ethyl acetate (1500 ml×2) and the extracts pooled, washed with saturated bicarb. (1000 ml) and water (500 ml). After drying over MgSO, the ethyl acetate was evaporated under reduced pressure to give crude 2-(4-nitrophenyl) butyronitrile as a yellow oil, crude yield 138 g, 98%. Analysis by GC.MS indicated a para:meta ratio of 3.5:1.

EXAMPLE 11B

Methyl 4-cyano-4-(4-nitrophenyl)hexanoate

A mixture of 2-(4-nitrophenyl)butyronitrile (10.0 g), butanol (10 ml) and methyl acrylate (5.2 ml) was cooled to 10° C. in a 100 ml 3-necked round-bottomed flask, equipped with a magnetic follower. A solution of potassium tert-butoxide (0.6 g) in tert-butanol (10 ml) was added dropwise, maintaining the temperature at approximately 10° C. (solution turns purple). After addition was complete, the mixture was allowed to reach ambient temperature and then stirred for a further 2 hours. The reaction was worked-up by partitioning between diethyl ether (400 ml) and 1M $KH_2PO_4$ (400 ml). The ether layer was washed with water (50 ml), dried ($MgSO_4$) and concentrated under reduced pressure to yield methyl 4-cyano-4-(4-nitrophenyl)hexanoate (14.1 g, 99%) as an orange oil.

EXAMPLE 12

A 1 l jacketed biotransformation vessel was charged with 0.05M $KH_2PO_4$, pH 7.5 (500 ml) and methyl 4-cyano-4-(4-nitrophenyl)hexanoate (20 g, 72 mmol). α-Chymotrypsin (ex. Aldrich; 4 g) was introduced and the mixture was agitated using an overhead stirrer. Temperature was maintained at 37° C. with the aid of a thermocirculator and the pH controlled by a probe linked to an autotitrator. The biotransformation was allowed to proceed until 18 ml of 1M NaOH had been added (equivalent to 50% conversion). This took about 68 hours, with addition of more α-chymotrypsin (1 g portions) after 24 hours and 50 hours. At this point, the biotransformation was quenched by the addition of NaCl (50 g) and the resulting mixture was extracted with diethyl ether (500 ml×3). The extracts were pooled, dried and concentrated under reduced pressure, yielding 10 g (50%) of (R)-methyl 4-cyano-4-(4-nitrophenyl)hexanoate, enriched in the (R)-enantiomer, 70% ee by chiral HPLC analysis.

EXAMPLE 13

Nitroglutethimide (R)-methyl 4-cyano-4-(4-nitrophenyl)hexanoate (Example 5; 10 g, 36 mmol), enriched in the (R)-enantiomer to approximately 70% ee, was dissolved in glacial acetic acid (30.0 ml) contained in a 25 ml round-bottomed flask. The resulting mixture was heated to 60° C. with the aid of an oil bath followed by dropwise addition of conc. $H_2SO_4$ (15.0 ml). The solution was then heated at 100° C. for 30 minutes before pouring onto ice (100 g). The pH was adjusted to 6 using 5M NaOH and the mixture was then extracted with dichloromethane (3×200 ml). The extracts were pooled, dried (over $MgSO_4$) and concentrated under reduced pressure, giving (R)-nitroglutethimide of approximately 70% ee (8.3 g, 88%) as a brown oil.

EXAMPLE 14

(R)-Aminoglutethimide

A 3-necked round-bottomed flask was charged with (R)-nitroglutethimide (ca. 70% ee, 8.3 g, 32 mmol), 90% ethanol (250 ml) and $PtO_2$ (0.35 g). The vessel was then evacuated and charged with nitrogen. The mixture was stirred vigorously and subjected to $H_2$ at atmospheric pressure supplied via a balloon. The catalyst was removed by filtration through celite and the solvent removed under reduced pressure to give (R)-aminoglutethimide (ca. 70% ee, 7.1 g, 96%) as a pale brown solid.

EXAMPLE 15

A loopful of *Candida rugosa*, ATCC 10571, was used to inoculate 50 ml of sterile pH 6.0 aqueous medium [containing (g/l) yeast extract (5), $(NH_4)_2SO_4$ (1), $KH_2PO_4$ (5), $MgSO_4.7H_2O$ (0.2) and glucose (10)] in 500 ml Erlenmeyer flasks shaken at 250 rpm with a one inch (25 mm) throw for 24 hours at 25° C. The cells were then harvested by centrifugation at 1200 g for 10 minutes. The cells were resuspended to one fifth of their original harvest volume in 50 mM potassium phosphate pH 6.0. A 50 mg/ml emulsion of ethyl 4-cyano-4-(4-nitrophenyl)hexanoate in 50 mM potassium phosphate+0.1% Tween 80 was prepared by sonication for 10 minutes (cycles of 10 seconds on, 3 seconds off) at an amplitude of 18 μm in a Soniprep 150. 400 μl of this substrate emulsion was added to 1.6 ml of the resuspended cells in a 20 ml glass vial. The biotransformation reaction mixture was then incubated with shaking at 25° C., 250 rpm for 69 hours. After this time the reaction was stopped by the addition of 2 ml ethyl acetate. The sample was then analysed for enantiomeric excess by chiral HPLC (Chiralpak AD column; mobile phase 98.3% heptane-1.7% isopropyl alcohol; flow rate was 2 ml/min). The quenched reaction mixture was shaken vigorously and allowed to separate and the ethyl acetate layer pipetted off. Anhydrous magnesium sulphate was added. The dried ethyl acetate was transferred to a fresh vial and 25 μl trimethylsilyl diazomethane was added. The sample was mixed and left to stand for an hour at ambient temperature prior to HPLC analysis, which indicated >99% ee (R)-4-cyano-4-(4-nitrophenyl)hexanoic acid was produced in the biotransformation, with residual substrate ee of 24%, conversion 19%.

EXAMPLE 16

*Fusarium oxysporum* IMI 329662 was cultured on 25 ml of sterile pH 6.0 aqueous medium [containing (g/l) yeast extract (20), $(NH_4)_2SO_4$ (4), $KH_2PO_4$ (5), $MgSO_4.7H_2O$ (0.3), $Na_2HPO_4.2H_2O$ (5), $CaCl_2.2H_2O$ (0.2) and glucose (40)], in 250 ml point-baffled Erlenmeyer flasks shaken at 250 rpm with a one inch (25 mm) throw for 72 hours at 25° C. Cells were harvested, resuspended to original volume in 50 mM potassium phosphate and used in biotransformation as in Example 15. The biotransformation was stopped after 24 hours and chiral HPLC analysis was carried out as described in Example 15. This indicated 95.9% ee (R)-4-cyano-4-(4-nitrophenyl)hexanoic acid was produced in the biotransformation.

EXAMPLE 17

*Penicillium pinophilum* IMI 114933 was cultured as described in Example 16 but with the inclusion of 10 g/l tributyrin in the medium. Cells were harvested, resuspended to original volume in 50 mM potassium phosphate and used in biotransformation as in Example 15. The biotransformation was stopped after 24 hours and chiral HPLC analysis was carried out as described in Example 15. This indicated 89% ee (R)-4-cyano-4-(4-nitrophenyl)hexanoic acid was produced in the biotransformation.

CHART A
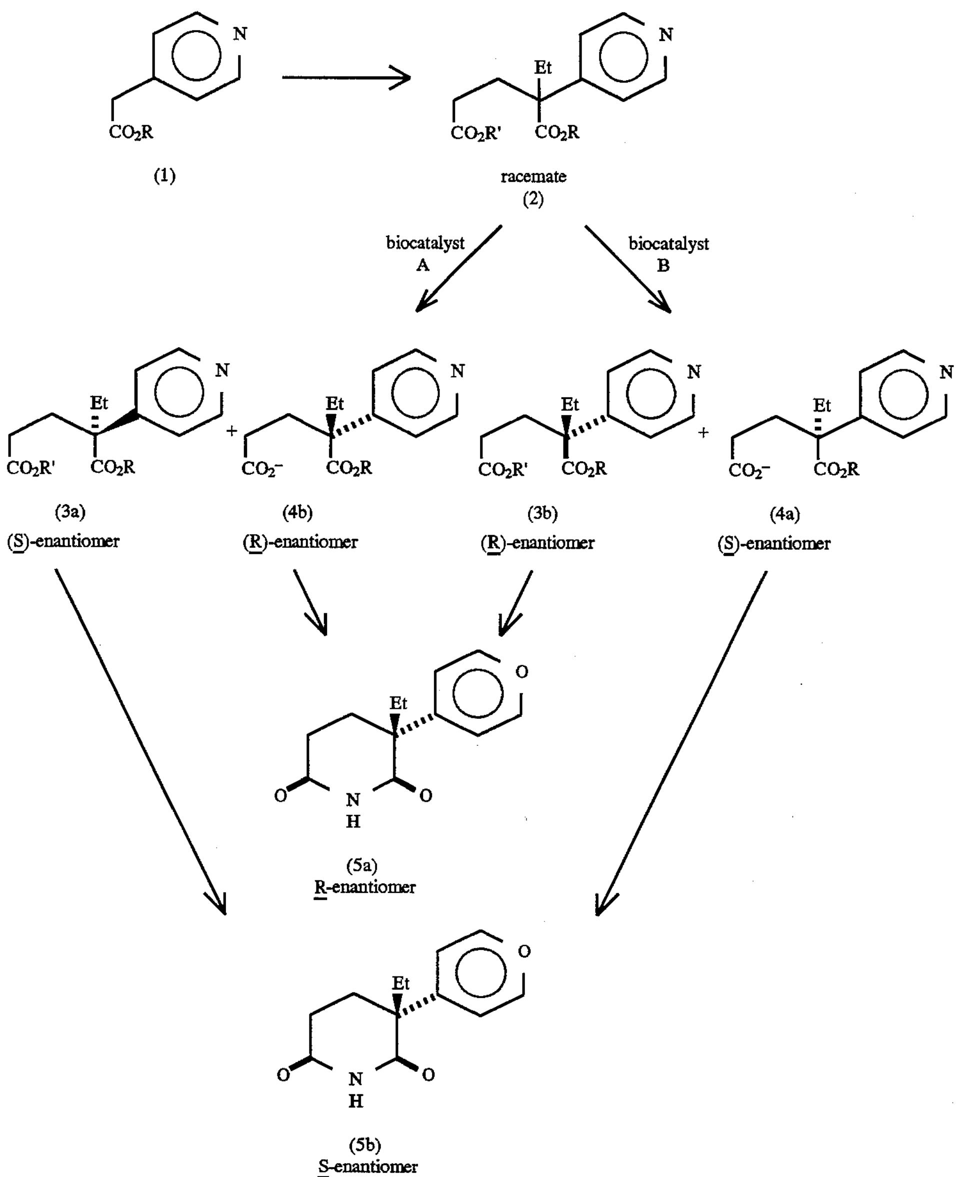
CHART B
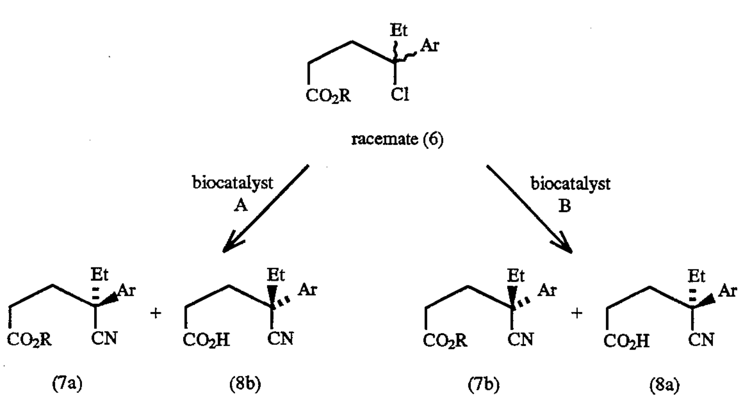

-continued (S)-enantiomer (R)-enantiomer (R)-enantiomer (S)-enantiomer

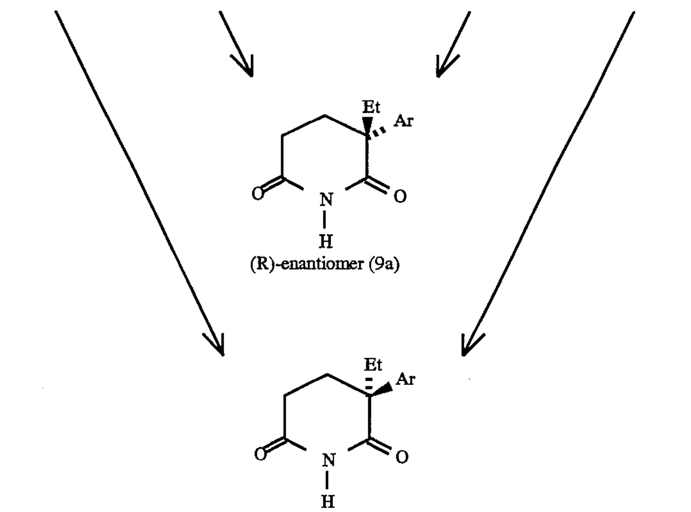

(R)-enantiomer (9a)

(S)-enantiomer (9b)

What we claim is:

1. A method of achieving enantioselective hydrolysis of a glutarate ester, comprising the steps of contacting a compound of formula II

II

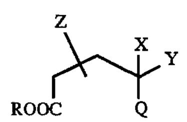

wherein: Q is CN or COOR'; R is an esterifying radical; R' is H or an esterifying radical; X and Z independently are H or an optionally substituted $C_1$–$C_{10}$ straight or branched chain alkyl, aralkyl or aryl group; and Y is an optionally substituted aryl, carbocyclic, or heterocyclic group containing up to 12 carbon atoms;

with an enantioselective esterase which enantioselectively hydrolyzes the COOR group of one enantiomer of said ester, producing a product having an enantiomeric excess of at least 50%.

2. A method according to claim 1, wherein Q is COOR'.

3. A method according to claim 2, wherein X and R' are each a $C_{1-10}$ alkyl group, and R is H or $C_{1-10}$ alkyl.

4. A method according to claim 3, wherein X is ethyl.

5. A method according to claim 2, wherein Y is 4-pyridyl.

6. A method according to claim 2, wherein Z is H.

7. The method according to claim 1, wherein said enantioselective esterase is selected from the group consisting of Aspergillus acylase I, esterase 30,000, Rhizopus Japonicus lipase, F3 lipase, porcine pancreas A2 lipase, Candida F6 lipase, pig liver esterase, CE lipase, AY lipase, α-chymotrypsin, *Candida cyclindracae* lipase, and esterase derived from *Candid rugosa, Fusarium oxysporum* IMI 329662, *Penicillium pinophilum* IMI 114933, P3U1 NCIMB 40517, Trichosporon ENZA I-3 IMI 348917, and *Ophiostoma novo-ulmi* IMI 356050.

8. The method according to claim 1, further comprising separating and cyclizing the hydrolyzed acid product of said enantioselective hydrolysis reaction to produce a glutarimide of formula I

I

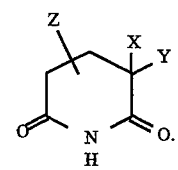

9. The method according to claim 1, further comprising separating and cyclizing the enantioselectively enriched unhydrolyzed ester product of said enantioselective hydrolysis reaction to produce a glutarimide of formula I

I

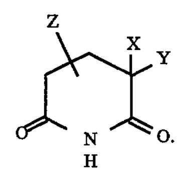

10. The method according to claim 9, wherein Q is COOR' and cyclisation comprises reacting with ammonia.

11. A method according to claim 2, wherein the compound of formula I is (R)-4-pyridoglutethimide.

12. A method according to claim 2, wherein R and R' are each methyl or ethyl.

13. A method according to claim 8, wherein Q is COOR' and cyclization comprises reaction with urea.

14. A method according to claim 1, wherein Q is CN.

15. A method according to claim 14, wherein X is $C_{1-10}$ alkyl, and R is H or $C_{1-10}$ alkyl.

16. A method according to claim 15, wherein X is ethyl.

17. A method according to claim 13, wherein R is methyl or ethyl.

18. A method according to claim 14, wherein Z is H.

19. A method according to claim 14, wherein Y is 4-pyridyl, phenyl, 4-nitrophenyl or optionally N-protected 4-aminophenyl.

20. A method according to claim 8, wherein Y is 4-nitrophenyl, further comprising the step of reducing said nitrophenyl group to produce a 4-aminophenyl group.

21. A method according to claim 14, wherein the compound of formula I is (R)-4-pyridoglutethimide or (R)-aminoglutethimide.

22. A method according to claim 9, wherein Q is CN and cyclization comprises heating in an acidic medium.

* * * * *

UNITED STATES PATENT AND TRADEMARK OFFICE

CERTIFICATE OF CORRECTION

PATENT NO. : 5,661,014

DATED : August 26, 1997

INVENTOR(S) : Christopher Thomas Evans et al.

It is certified that error appears in the above-indentified patent and that said Letters Patent is hereby corrected as shown below:

Claim 11, line 1, please delete "2" and insert therefor --8--.

Claim 21, line 1, please delete "14" and insert therefor --9--.

Signed and Sealed this

Twenty-first Day of October 1997

Attest:

BRUCE LEHMAN

*Attesting Officer* *Commissioner of Patents and Trademarks*